United States Patent [19]

Underhill et al.

[11] 4,042,681

[45] Aug. 16, 1977

[54] COMPOSITE ATTRACTANT FOR BERTHA ARMYWORM MOTH

[75] Inventors: Edward W. Underhill; Melvin D. Chisholm; Warren F. Steck; Berton K. Bailey; Peter M. Lamb, all of Saskatoon; Dean L. Struble; G. Edward Swailes, both of Lethbridge, all of Canada

[73] Assignee: Canadian Patents and Development Limited, Ottawa, Canada

[21] Appl. No.: 643,597

[22] Filed: Dec. 22, 1975

[51] Int. Cl.² .............................................. A01N 17/14
[52] U.S. Cl. .......................................... 424/84; 43/133
[58] Field of Search ............................ 424/84; 43/133

[56] References Cited
PUBLICATIONS

Jacobson; M. "Insect Sex Pheromones," (1972), pp. 224–231.
Chemical Abstracts, vol. 83, (1975), p. 109749r.

Primary Examiner—V. D. Turner
Attorney, Agent, or Firm—Alan A. Thomson

[57] ABSTRACT

Mixtures of two compounds Z-11-hexadecen-1-ol acetate (A) and Z-9-tetradecen-1-ol acetate (B) exhibit high and species specific attractancy for the male Bertha Armyworm moth. The optimum attractant and specificity effect has been observed at proportions of about 95% A and 5% B. A dose of about 0.1 to 10 mg of the attractant per insect trap has been found effective. Neither A nor B alone are good attractants for the Bertha moth, although A alone has slight attractancy.

8 Claims, No Drawings

COMPOSITE ATTRACTANT FOR BERTHA ARMYWORM MOTH

FIELD OF THE INVENTION

Insect sex attractants (pheromones) are provided which exhibit high and species specific attractancy for the Bertha Armyworm moth (*Mamestra configurata*).

DESCRIPTION OF THE PRIOR ART

In order to detect substantial populations of insect pests, reliable sampling techniques are required. Recently, insect sex attractants or pheromones have been discovered for a number of insect species (moths) and these attractants have been used to trap the male moths of the species thus permitting a reliable estimate of the insect population to be made. Where no chemical attractant was known, illuminated traps or traps baited with live female moths of the species have been used. It is difficult and expensive to provide the female moths at many sampling locations. The illuminated traps are expensive and non-specific, i.e. most other night flying insects are also trapped.

These techniques have been applied to the Bertha Armyworm moth with limited success (the Bertha Armyworm is a significant pest of field crops, particularly rape, in mid-western and some other parts of North America). Alternatively, bertha pupae have been dug from the ground and counted. This method is time-consuming and tedious, and has proved unsatisfactory: live and dead pupae cannot be differentiated readily, and variables of weather and predator (or parasite) populations cannot be evaluated well enough to allow accurate predictions of the larvae population later on. The bertha larvel stage may itself be counted, but this method is "after the fact" and therefore of limited practical value. The appearance of Bertha Armyworms is generally so sudden as to give little warning. Use of a chemical attractant would be more satisfactory.

The chemical attractant possessed by the female bertha moths is not fully known. The compound z-9-tetradecen-1-ol acetate has been prepared synthetically and is known as a part of the sex attractant systems of some insects (Bryotopha sp., the southern armyworm moth, the diamondback moth, the lesser sea tortrix and other moths of the family Noctuidae). This compound is unattractive in itself to bertha moths.

Recently, M. D. Chisholm et al found that one component of the natural sex pheromone of the Bertha Armyworm is Z-11-hexadecen-1-ol acetate. In itself, this compound does not significantly attract bertha moths to field traps, although some action on male bertha moths can be demonstrated under laboratory conditions. This compound has not previously been shown to be a natural sex pheromone of any insect.

SUMMARY OF THE INVENTION

We have now found that a mixture comprising a major proportion of Z-11-hexadecen-1ol acetate (A) with a minor proportion of Z-9-tetradecen-1-ol acetate (B) is an effective attractant for male Bertha moths. Amounts of B of at least about 1% of A plus B will show effective attraction with the attraction peaking at around 5% B. At 10% B, the attraction observed was less that at 5% in almost all cases. Some attraction was still evident at 50% B but equivalent amounts of moths of other species were being attracted, i.e. the mixture was not species specific. The 95% A plus 5% B mixture has shown high species specificity. Mixtures close to this optimum ratio attract only male bertha moths, whereas other ratios attract, in addition, males of non-economic species.

This invention opens the way to inexpensive monitoring of this insect pest on an intensive scale, and possibly to control of local outbreaks by mass trappings or disruption of reproductive mating.

The preparation of A has apparently not been described in the literature. A synthesis has been developed in our laboratories starting with 10-chloro- or 10-bromo-decanol, forming the tetrahydropyranyl ether, reacting this ether with lithium acetylide to produce the tetrahydropyranyl ether of 11-dodecyn-1-ol, reacting this dodecynol derivative with a metal amide and with butyl bromide to produce after hydolysis or acetylation 11-hexadecyn- 1-ol or 11hexadecyn-1-ol acetate respectively. Catalytic reduction over a suitably deactivated catalyst afforded Z-11-hexadecen-1-ol (or its acetate). The alcohol was acetylated by standard techniques to the acetate. This synthesis is believed particularly advantageous but other routes are possible. The Z isomer was obtained in about 30% yield, with less than about 2% of the E isomer present. We have determined that small quantities of the E isomer, e.g. up to about 15%, do not significantly inhibit the attractancy of the mixture of the invention.

Compound B is now commercially available. Again we have determined that the presence of small quantities ($\leq 15\%$) of the E isomer of B does not significantly inhibit the attractancy of the mixture. Thus complete isomeric resolution of the synthesized compounds is not required, allowing use of a less costly product.

We have found that about 1 mg of attractant is a convenient and effective dose for each trap. With 10 mg or more, a suppression of attraction takes place, while with less than 0.1 mg the duration of attractancy becomes somewhat too short as the attractant is then exhausted after only three weeks. No fillers or other ancillary compounds are required.

The attractant mixture is normally used by itself but inert diluents, fillers or carriers may optionally be present. The mixture may be dissolved in and dispersed from an inert volatile solvent, e.g. a lower alkane or alkanol. The solvent then evaporates leaving a residue of the mixture to slowly volatilize and exert its attractant effect. Any inert solids such as siliceous materials, aluminas etc may be used as fillers or carriers. A polymeric substrate or container may be used to expose the mixture. Non-volatile inert liquids may serve as diluents or "keepers" reducing the volatility and prolonging the attractant effect. Such inert liquids may be for instance, vegetable oils and mineral oils, e.g. rapeseed oil, corn oil, olive oil, and pharmaceutical grade refined mineral oil. With these "keeper" liquids, the traps can be loaded with larger amounts of attractant giving longer trap life without significant suppression of attraction. For example, when rape crops are being monitored rapeseed oil would be a very suitable diluent and "keeper".

DESCRIPTION OF PREFERRED EMBODIMENTS

The data following were obtained using cylindrical plastic traps about 30 cm long and 12 cm in diameter. Each end of the cylinder was covered by an inward-pointing cone of screening with a hole 1.0–1.2 cm in diameter at the apex to allow entry of moths. The chemical attractants for the moth were enclosed in a hollow polypropylene cap placed, by means of tape or a wire, at the center of the cylinder. The traps were tied horizontally to fence posts or other supports at a height of approximately 1 meter from the ground. The test traps were inspected for Bertha Armyworm moths daily or semi-weekly as circumstances dictated. Several other trap designs were also tested and found satisfactory.

EXAMPLE 1

Although the natural populations of the Bertha Armyworm remained extremely low in our test area, we were able to capture during July over 50 specimens (male berthas) using five baited traps set out at several sites within two miles radius of Saskatoon. The traps were baited with 1.0 mg of A plus B in the proportion 95/5 respectively, without any additional materials. A black-light trap of the kind currently used for attracting bertha moths attracted in the same area only 4 specimens. The baited polypropylene cap provided high attractancy throughout the entire flight period of the bertha moth.

EXAMPLE 2

Using traps baited with 2 mg of the mixture in the proportion 90A/10B in a field trial near Winnipeg, Manitoba, about 5% of the total possible number of released berthas were recaptured by the pheromone traps as compared with 1.4% recaptured by black-light traps. A recapture rate of 0.1% has been considered acceptable. In this experiment, 26,000 moths (equal numbers of males and females) were released.

EXAMPLE 3

Tests were carried out to recapture male bertha moths released into outdoor screen cages (20 × 10 × 7 feet) using traps baited with varying proportions of A (Z-11-hexadecenyl acetate) to B (Z-9-tetradecenyl acetate). The

EXAMPLE 5

The effect of the other isomers on the optimum 95/5 A/B lure mixture has been tested in recapturing 80 male moths released in outdoor screen cages (20 × 10 × 7 feet). Results are depicted in Table 3. At the 10% level, the presence of the E isomer of A or B allowed acceptable attraction. Similar results were obtained with the unesterified alcohol of B (either isomer). Thus up to about 15% of these impurities could be tolerated. With the unesterified alcohol of A as additive, the Z isomer gave indication of being a significant inhibitor or attraction. Relatively impure commercial preparations could be used with it being necessary to minimize the content of Z-11-hexadecenol impurity only.

TABLE 3

| Additive to 95/5 Mixture | Moths caught in 4 nights |
| --- | --- |
| 95/5 mixture (control) | 17 |
| 10% E-9-tetradecenyl acetate | 27 |
| 10% E-11-hexadecenyl acetate | 10 |
| 10% Z-9-tetradecenol | 12 |
| 10% E-9-tetradecenol | 20 |
| 10% Z-11-hexadecenol | 1 |
| 10% E-11-hexadecenol | 12 |

We claim:

1. A composite insect attractant for male Bertha Armyworm moths (*Mamestra configurata*) comprising:
   A. Z-11-hexadecen-1ol acetate, and
   B. Z-9-tetradecen-1-ol acetate wherein the proportions of A and B are within about 90–99% of A and about 10–1% of B.
2. The composite attractant of claim 1 wherein the relative amounts of A and B are about 95% and 5% respectively.
3. The composite attractant of claim 1 including, in addition, up to about 15% by weight of A plus B of the isomer E-11-hexadecen-1-ol acetate.

TABLE 1

| Attractant composition | 115 males released 3 nights' catch | 82 males released 3 nights' catch | 121 males released 4 nights' catch | 78 males released 5 nights' catch |
| --- | --- | --- | --- | --- |
| 90% A + 10% B | 9 | 1 | 9 | 11 |
| 95% A + 5% B | 6 | 9 | 17 | 14 |
| 97% A + 3% B | 7 | 7 | 9 | 3 |
| 99% A + 1% B | 2 | 1 | 3 | 0 |
| Date (1975) | 12–15 Aug. | 15–18 Aug. | 18–22 Aug. | 22–27 Aug. |
| Mean temp. at flight period: | 10° C | 6° C | 12° C | 9° C |
| Recapture rate | 21% | 22% | 31% | 36% |

EXAMPLE 4

Tests were conducted using varied ratios of A and B in single traps. Different ratios of the Z and E isomers of A were used in three tests. Results are shown in Table 2.

TABLE 2

| 11-hexadecenol acetate (A) | 9-tetradecenol acetate (B) | Bertha Moths | Other species Moths |
| --- | --- | --- | --- |
| nil | 100% (all Z) | nil | nil |
| 5% (all Z) | 95% (all Z) | nil | 9 |
| 10% (all Z) | 90% (all Z) | nil | 11 |
| 50% (all Z) | 50% (all Z) | nil | 29 |
| 90% (all Z) | 10% (all Z) | 3 | 4 |
| 95% (all Z) | 5% (all Z) | 14* | nil |
| 100% (all Z) | nil | nil | nil |
| 90% (5:4 Z:E) | 10% (all Z) | 4 | 7 |
| 70% (3:4 Z:E) | 30% (all Z) | nil | 18 |
| 90% (2:7 Z:E) | 10% (all Z) | nil | 3 |

*The species specificity of mixture 95A/5B was confirmed in separate trials.

4. The composite attractant of claim 1 including, in addition, up to about 15% be weight of A plus B of the isomer E-9tetradecen-1-ol acetate.
5. The composite attractant of claim 1 including up to about 15% of A plus B of the alcohols 9tetradecenol and E-11-hexadecenol.
6. The composite attractant of claim 1 including an inert oil diluent.
7. An insect trap for male moths of the Bertha Armyworm baited with an attractant as in claim 1 wherein the amount of the attractant present is from about 0.1 to 10 mg.
8. An insect trap for male moths of the Bertha Armyworm baited with an attractant as in claim 1 wherein the amount of the attractant is at least about 10 mg and an inert oil diluent is present.

* * * * *